US007695707B2

(12) United States Patent
Ghosh et al.

(10) Patent No.: US 7,695,707 B2
(45) Date of Patent: Apr. 13, 2010

(54) IODIZING AGENT AND PROCESS FOR PREPARATION THEREOF

(75) Inventors: Pushpito Kumar Ghosh, Gujarat (IN); Satish Hariray Mehta, Gujarat (IN); Jatin Rameshchandra Chunawala, Gujarat (IN); Mrunalben Vinodray Sheth, Gujarat (IN); Mahesh Ramniklal Gandhi, Gujarat (IN)

(73) Assignee: Council of Scientific and Industrial Research, New Delhi (IN)

( * ) Notice: Subject to any disclaimer, the term of this patent is extended or adjusted under 35 U.S.C. 154(b) by 1564 days.

(21) Appl. No.: 10/879,510

(22) Filed: Jun. 30, 2004

(65) Prior Publication Data

US 2006/0003024 A1    Jan. 5, 2006

(51) Int. Cl.
*C07F 11/00* (2006.01)
(52) U.S. Cl. ............... 423/499.4; 423/115; 423/126; 423/128; 423/147
(58) Field of Classification Search ............... 423/499, 423/419; 424/499.413
See application file for complete search history.

(56) References Cited

U.S. PATENT DOCUMENTS 5,362,457 A * 11/1994 Grubbs et al. ............ 423/115
5,776,424 A * 7/1998 Martin et al. ............ 423/593.1

5,814,291 A * 9/1998 Kelkar ............ 423/395

OTHER PUBLICATIONS

LL Diosady, J.O. Alberti, M.G. Ventakesh Mannar, and S. FitzGerald. Stability of iodine in iodized slat used for correction of iodine-deficiency disoroders.II.*
Adding an oxidant increases the stability of iodine in ioized salt by Huimin Shi. Food and Nutrition Bulletin. vol. 25, 2004. The United nations University.*
Adsorption behavior of IO3 by Co3 and No3 hydrotalcite by Takashi Toraishi. Applied Clay Science 22920020 17-23.*
The Stability of Potassium Iodate in Cride table Salt. by Guillermo Arroyave, Ph.D. 1956.*
International Search Report, (Feb. 2005).
Toraishi et al., "Adsorption Behavior of I03- and C032- and N03—Hydrotalcite", Applied Clay Science, vol. 22, 2002, pp. 17-23, XP002318031.
Arroyave et al, "The Stability of Potassium Iodate in Crude Table Salt", Bulletin World Health Organisation, vol. 14, 1956, pp. 183-185, XP002318030.

* cited by examiner

*Primary Examiner*—Melvin C Mayes
*Assistant Examiner*—Colette Nguyen
(74) *Attorney, Agent, or Firm*—Nixon & Vanderhye, P.C.

(57) ABSTRACT

A method for preparation of iodizing agent for the use in the formulation of iodized salt that offers excellent stability of iodine in iodized salt is developed and the unrefined salt iodized with this compound was tested for its stability in presence of moisture, temperature and metal salts at higher temperature. The hydrotalcite type layered compound was used to prepare such compound and part of carbonate was substituted with iodate anion. The iodizing agent exhibited excellent stability of iodine in iodized salt.

10 Claims, No Drawings

IODIZING AGENT AND PROCESS FOR PREPARATION THEREOF

FIELD OF THE INVENTION

The present invention relates to a novel iodizing agent. The present invention also relates to a novel process for the preparation of the iodizing agent from Pharma grade hydrotalcite and water soluble alkali iodate by intercalating iodate anion in the interlayer space. The iodizing agent so prepared is stable and can be effectively used in the formulation of iodized salt, wherein it offers stability to iodine.

BACKGROUND OF THE INVENTION

Iodine is a very important trace element necessary in the biosynthesis of thyroid hormones. Iodine is required for developing and maintaining healthy body. There are well known Iodine Deficiency Disorders like Goiter and Cretinism. The edible salt is chosen as a vehicle in the provision of iodine because of its uniform consumption and availability to all segments of population independent of social or economic status. During the past twenty years, there has been a strong effort, lead by the United Nations, to iodize all salt for human consumption. Potassium iodate and potassium iodide are most often used in iodizing the edible salt. The Food and Nutrition Board of National Research Council of the USA placed the optimum requirement of iodine at 150-300 µg per day, and considering 10 gm of salt consumption per day, the iodisation level of salt could be around 15-30 mg per kg of salt. The impurities present in edible salt, moisture and temperature are some of the main factors that induce loss of iodine from iodized salt. In order to deliver adequate amount of iodine to the consumer while avoiding the unnecessary excess addition of iodizing agent in salt that is normally done to compensate for losses, it is of paramount importance that an ultrastable iodizing agent should be developed. This would allow a simultaneous benefit in as much as it may not be necessary to purify salt excessively as is the practice at present to minimize iodine loss apart from imparting a superior aesthetic effect such as free flow nature. The latter is especially important, as it is well known that impurities such as magnesium are required as micronutrient and can also enhance the saltiness of salt.

Reference may be made to a paper entitled "Stability of iodine in iodized salt" by L. L. Diosady and Venkatesh Mannar, published in *The Proceedings of 8th World Salt Symposium,* 2000, Volume 2, pp 977-982, wherein it is stated in the abstract that, "since iodine readily sublimes at ambient temperature, the effectiveness of salt iodisation programs depends on the stability of the iodine carrier, typically potassium iodate." The authors further state that they examined the stability of iodine in typical salts available in 12 countries in a controlled laboratory setting, at 40° C. and controlled humidity (60 or 100%) for periods up to 12 months. Iodine was rapidly lost in most unrefined salt samples. Further, the presence of moisture due to hygroscopic impurities, and metal ion impurities, such as iron accelerated the loss of iodine.

Reference may be made to a paper entitled "Stability of iodized salt with respect to iodine content" by S. A. Chauhan et al. in *Research and industry, March* 1992, Vol 37, pp 38-41 wherein stability of iodine in iodized salt prepared by submersion method using solution of potassium iodate was studied for iodized salt packed in HDPE bags, for iodized salt exposed to atmosphere, iodized salt solution on boiling and iodized salt under heating up to 120° C. The draw back associated with this work evinces that there is considerable loss of iodine during storage in bags or in open atmosphere. Moreover, significant loss of iodine is observed on boiling the salt solution or heating the iodised salt.

Reference may be made to a paper entitled "The stability of potassium iodate in crude table salt", by Arroyave, G. et. al., in *Bull. World Health Organisation,* 1956, 14, pp 183-155, wherein potassium iodate was stabilized by calcium carbonate in crude sea salt stored in hemp fiber sacks for up to eight months at ambient temperatures and relative humidity between 70 and 84%. Only some 3.5% of added iodine was reported to be lost. The main draw back is that the stability of iodine under exposure to atmosphere and under variable temperature has not been studied. However, as is well known to practitioners in this field, this is not the approach followed in practice for stabilization, presumably because the results are not as encouraging as that indicated in the above report.

Reference may be made to a paper entitled "Micro encapsulation for iodine stability in salt fortified with ferrous fumarate and potassium iodide" by Diosady L. L. et. al., in *Food Research International,* 2002, Volume 35, Issue 7, pp 635-642 wherein potassium iodide and potassium iodate were encapsulated in modified starches, gelatin, sodium hexametaphosphate and purified sodium chloride by spray drying and fluidized bed drying to produce microcapsules containing 0.3 to 2% iodine. The most stable combination, containing 50 mg iodine and 1000 mg iron per kg salt, retained more than 75% of the added iodine for a year at 40° C., 100% RH. The authors have not given data on stability of iodine for singly fortified salt but even if it were very stable, the process of micro encapsulation is expensive.

Reference may be made to the paper entitled "Synthesis, thermal investigations and solubility of a new double salt $K_2Mg(IO_3)_4 \cdot 2H_2O$" by D. Rabadjieva and M. Maneva in *Thermochimica Acta,* 1997, Vol 293, pp 117-123, which describe the thermal properties of the new $IO_3$-containing double salt. There is no mention of its suitability, if any, as an iodizing agent. Moreover, the high local concentration of iodine would make it difficult to guarantee uniform distribution in the product while ensuring a total iodine not exceeding 30 ppm.

Reference may be made to the paper entitled "The properties of salt-filled sodalites. Part 4. Synthesis and heterogeneous reactions of iodate-enclathrated sodalite." By Joseph Christian Buhl, in "*Thermochimica Acta,* 1996, Vol 286, pp 251-262, where in sodalite solid solution $Na_8[AlSiO_4]_6(IO_3)_{2-x}(OH.H_2O)_x$; (0.7<x<1.3) is produced from the system $Na_2O—2SiO_2—Al_2O_3—NaIO_3—H_2O$ under hydrothermal conditions. The main disadvantage of this kind of compound for its use as iodising agent in the preparation of iodised salt is its high alkalinity that would make it unsuitable in pharmaceutical or food application. Further, the concentration of iodate in this compound is too high for even distribution in edible salt.

Reference may be made to the paper entitled "Anionic clay minerals" by W. T. Reichle, in *Chemtech,* January 1986, pp 58-63 which describes the structure and properties of hydrotalcites which are layered anionic clays bearing the chemical composition $[Mg_6Al_2(OH)_{16}CO_3 \cdot 4H_2O]$. These materials are used widely in antacid formulations as well as other applications such as halogen scavenger, adsorbent for wastewater treatment, stabilizer in poly-vinyl chloride and fire-retardant. There is no report however of the use of such materials for the preparation of iodizing agent.

Reference may be made to the paper entitled "Adsorption behavior of $IO_3^-$ by $CO_3^{2-}$ and $NO_3^{2-}$—hydrotalcite" by Takashi Toraishi et. al. in *Applied Clay Science,* 2002, 22, pp 17-23, wherein the adsorption behavior of iodate by hydrotalcite type compounds with $CO_3$ ($HTCO_3$) and $NO_3$ ($HTNO_3$) was studied for their application in removal of iodine from radioactive waste for disposal. The authors found that $HTNO_3$ can adsorb iodate but no mention is made of the possible use of such methodology for preparation of iodizing agent. Moreover, $HTNO_3$ is not recommended for edible purpose.

Reference may be made to P.M.Oza et. al. in Indian patent application No. 1053/DEL/2000, where in an improved process for the preparation of Hydrotalcite from bittern-mother liquor left after separation of salt has been disclosed. The hydrotalcite contains carbonate anion and no attempt was made to substitute the carbonate with other anions.

Reference may be made to the paper entitled "The use of Hydrotalcite as an anion adsorbent" by Linda M. Parker et. al. in *Ind. Eng. Chem. Res.* 1995, 34, pp 1196-1202 where in use of fired and non fired $HTCO_3$ for adsorption of anions like $Cl^-$, $Br^-$, $NO_3^-$, $HPO_4^-$, $SO_4^-$ and borate was studied carried out. However, there is no mention of any study with iodate anion.

OBJECT OF THE INVENTION

The main object of the present invention is to provide a process for the preparation of novel iodizing agent, which obviates the drawbacks as detailed above.

Another object of the present invention is to sequester the iodate anion in the iodizing agent in its matrix to prevent the chemical degradation in presence of moisture and chemical impurities such as $MgCl_2$ in the salt.

Still another object of the present invention is to promote the use of salt containing beneficial impurities for the body while at the same time reducing cost of purification of salt and maintaining the iodizing agent in stable form.

Yet another object of the present invention is to utilize the iodine-containing iodate anion as the iodizing agent as practiced in many tropical countries such as India.

Yet another object of the present invention is to enhance the stability of the iodate anion and protect it from direct exposure by incorporating it in the interlayer space of synthetic hydotalcite.

Yet another object of the present invention is to substitute a part of the carbonate anion in the synthetic hydrotalcite with iodate anion.

Yet another object of the present invention is to intercalate iodate anions available in the solution, in the interlayer space of hydrotalcite by thermal decomposition of the carbonate anion in synthetic hydrotalcite.

Yet another object of the present invention is to make use of water-soluble alkali iodate.

Yet another object of the present invention is to intercalate iodate anion into synthetic hydrotalcite with iodine content in the range of 0.5-10.0% (w/w).

Yet another object of the present invention is to intercalate more than 85% of the total iodate taken for the intercalation reaction.

SUMMARY OF THE INVENTION

The aim of the present invention is directed to provide a novel process for the preparation of an iodizing agent with iodine content in the range of 0.5 to 10.0% (w/w). The Pharma grade synthetic hydrotalcite having (i) $MgO:Al_2O_3$ molar ratio in the range of 7.7 to 4.6; (ii) XRD pattern with intensity peaks (A°) 7.77, 3.87, 2.57, 1.53, and 1.42; (iii) and sharp IR absorption peak at ca. 1360 $cm^{-1}$ was used for the preparation of a stable iodizing agent. The calculated amount of hydrotalcite was, prior to interaction with potassium iodate solution, at appropriate temperature and under continuous stirring, was powdered to desired size, calcined and cooled. During the reaction, the temperature of the reaction was maintained between 60 to 80° C. for a period of about five minutes. The present process is rapid and cost effective giving highly stable iodizing agent. The solid agent can be obtained by simple filtration, drying and it obviates the need for any further purification step. This iodizing agent is useful for iodization of common salt where the loss of iodine in presence of moisture, metal salts and on exposure to high temperature is not affected.

Accordingly the present invention provides a method for the preparation of iodizing agent that offers stability of iodine in formulation of iodised salt, the method comprising:

(i) grinding pharma grade hydrotalcite to obtain hydrotalcite powder;

(ii) calcining the powdered hydrotalcite obtained in step (i);

(iii) cooling the calcined hydrotalcite to obtain solid synthetic hydrotalcite;

(iv) heating an aqueous potassium iodate solution;

(v) adding calculated quantity of the solid synthetic hydrotalcite obtained in step (iii) into the potassium iodate solution prepared in step (iv) under agitation for uniform dispersion;

(vi) maintaining the temperature in the range of 60 to 80° C. while stirring the reactants to obtain a slurry;

(vii) aging the slurry for a period between 30 to 60 minutes and intermittently stirring for 1 minute at an interval of 30 minutes for effective contact and substitution of anions in the interlayer space;

(viii) filtering the resultant slurry and washing the cake so obtained with distilled water to remove adhering salts therefrom;

(ix) drying the cake to get the iodizing agent.

In an embodiment of the present invention pharma grade synthetic hydrotalcite having $MgO:Al_2O_3$ molar ratio of in the range of 7.7 to 4.6; XRD pattern having intensity peaks (A°) 7.77, 3.87, 2.57, 1.53, 1.50, 1.42 and sharp IR absorption peak of interlayer carbonate ions at ca. 1360 $cm^{-1}$ is used for the preparation of stable iodizing agent.

In another embodiment of the present invention the synthetic hydrotalcite was ground to pass through 60 BSS mesh.

In yet another embodiment of the present invention, the iodate salt may be of water soluble alkali metal salts.

In still another embodiment of the present invention, the hydrotalcites may be calcined in the temperature arrange of 450° C. to 550° C. for 30 to 75 minutes followed by cooling to 60-80° C.

In still another embodiment of the present invention, the concentration of metal salt may be in the range of 0.005 to 0.022 molar.

In still another embodiment of the present invention, the aqueous solution was heated in the range 60-80° C. prior to addition of calcined synthetic hydrotalcite.

In yet another embodiment of the present invention the iodine content in the synthetic hydrotalcite was in the range of 0.5-10.0% (w/w).

In yet another embodiment of the present invention, the iodate-containing synthetic hydrotalcite was dried in an oven at 80-110° C. to expel all moisture.

In yet another embodiment of the present invention, the iodine content of the iodised salt using novel iodizing agent subjected to stability studies was 30 ppm.

DETAILED DESCRIPTION OF THE INVENTION

In accordance with the present invention, a modified hydrotalcite composition containing iodate anion is prepared and utilised for the preparation of iodized salt having greater stability of iodine. Hydrotalcite ($Mg_6Al_2(OH)_{16}CO_3.4H_2O$) is a naturally occurring mineral known for its antacid properties. However, natural form is not pure enough and occurs in small deposits. So, proprietary processes have developed synthetic hydrotalcite for pharmaceutical industry as antacid. Synthetic hydrotalcite is anionic clay. Here cationic layer is crystalline magnesium hydroxide (brucite) in which aluminium cation partially substitutes for magnesium cation. This substitution gives rise to a positive charge which is neutralised by exchangeable carbonate and/or sulphate anion in the anionic layer for synthetic hydrotalcite and magaldrate, respectively for their use in antacid formulations.

The hydrotalcite ($HTCO_3$) is prepared from magnesium rich bittern—the mother liquor left out after separation of salt from the brine by solar evaporation—by known technique in the prior art and grinding to pass through 60 BSS mesh. The synthetic hydrotalcite suitable for pharmaceutical application and having molar ratio of $MgO:Al_2O_3$ in the range of 7.7 to 4.6, XRD pattern having intensity peaks (A°) 7.77, 3.87, 2.57, 1.53, 1.50, 1.42 and sharp IR absorption peak of interlayer carbonate ions ca. 1360 $cm^{-1}$ was used for the preparation of stable iodizing agent.

The hydrotalcite powder is calcined at 450-550° C. for 30-75 minutes in a furnace to decompose the carbonate and drive off carbon dioxide. The calcined hydrotalcite is cooled to 60-80° C. A solution of potassium iodate having concentration in the range of 0.005-0.022M is prepared in distilled water and heated to 60° C.-80° C. to expel dissolved carbon dioxide. The calcined and cooled hydrotalcite is added to this solution at 60-80° C. and stirred for five minutes maintaining the said temperature. The stirring is given for one minute at an interval of 30 minute. After one hour, the slurry is filtered. The solid is washed with distilled water to, make it free from adhering electrolytes. The solid is dried at 80-110° C. The dried solid is ground and passed through 60 BSS mesh. The prepared hydrotalcite is mixed with solar salt to contain 30 ppm of iodine in the resultant salt.

The iodine estimation was carried out using classical method of iodometry. The analysis of magnesium content was carried out using EDTA complexmetry titration. Aluminium was estimated employing gravimetric method by precipitating as aluminum hydroxide and weighing the fired precipitates as $Al_2O_3$. Powder XRD pattern was taken in the range of $2\theta=5-70°$. IR spectra were taken using KBr pellets in the frequency range of 4000-400 $cm^{-1}$. Potassium ions were estimated using flame photometric technique.

The present invention relates to the preparation of a novel and stable iodizing agent suitable for iodine stability in iodised salt. This iodizing agent was prepared by intercalation of iodate ions, available from aqueous solution of alkali metal salt, in the interlayer space of synthetic pharma grade hydrotalcite. The method of the present invention does not require any special device and the use of spray technique, conventionally used for direct iodization of common salt dispensed with. The iodate ions in the interlayer space impart enhanced stability to iodine. In the present invention, the absorption of iodate ions, in the interlayer space of synthetic hydrotalcite, for enhanced stability, is not reported in the prior art. Besides, no reference is cited of the use of calcined hydrotalcite for preparing iodine stable iodizing agent. The inventive steps adopted in the present invention are (i) intercalation of iodate anions (85%) in the interlayer space of hydrotalcite obviates the need of direct iodization by conventional agent viz potassium iodate; (ii) the stability of iodine is maintained and it prevents the loss of iodine due to moisture, temperature and metal salt; (iii) absorption of iodate ions in the interlayer space of calcined hydrotalcite dispenses the use of microencapsulation of potassium iodide and potassium iodate in modified starch, gelatin, sodium hexa meta phosphate and purified sodium chloride; (iv) preparing iodizing agent in aqueous solution kept at 70° C. and at atmospheric pressure, dispenses with the need of hydrothermal treatment; (v) the iodizing agent can be dried at 80 to 100° C. and obviates the need of spray dying or fluidized bed drying.

The following examples are given as way of illustration and should not be construed to limit the scope of present invention.

Example-1

6 gm of hydrotalcite having molar ratio of $MgO:Al_2O_3$ equal to 6.0, XRD pattern having intensity peaks (A°) 7.77, 3.87, 2.57, 1.53, 1.50, 1.42, and sharp IR absorption peak of interlayer carbonate ions at 1370 $cm^{-1}$, was powdered to pass through 60 BSS mesh and calcined in a furnace at 500° C. for one hour. The calcined hydrotalcite was cooled to 65° C. This was added to 100 ml of 0.01M potassium iodate solution prepared in distilled water, which is heated to 70° C. prior to addition. The reacting mass was stirred for five minutes maintaining the said temperature and left to stand for one hour with intermittent stirring for one minute at an interval of 30 minute. The resultant slurry was filtered. The solid separated was washed with distilled water till the wash filtrate does not show any silver iodate precipitate with silver nitrate. The solids were dried at 110° C. The dry material was analyzed for its iodine content using classical method of iodometry employing sodium thiosulphate as titrant and found to contain 2.1% of iodine in it. The composite filtrate was analysed for its potassium iodate content and found to contain 11.7 mg of potassium iodate.

Example-2

6 gm of hydrotalcite having molar ratio of $MgO:Al_2O_3$ equal to 5.5, XRD pattern having intensity peaks (A°) 7.60, 3.82, 2.57, 1.53, 1.50, 1.42, and sharp IR absorption peak of interlayer carbonate ions at 1365 $cm^{-1}$, was powdered to pass through 60 BSS mesh and calcined in a furnace at 450° C. for one hour. The calcined hydrotalcite was cooled to 80° C. This was added to 50 ml of 0.005M potassium iodate solution prepared in distilled water which is heated to 80° C. prior to addition. The reacting mass was stirred for five minutes maintaining the said temperature and left to stand for one hour with intermittent stirring for one minute at an interval of 30 minute. The resultant slurry was filtered. The solid separated was washed with distilled water till the wash filtrate does not show any silver iodate precipitate with silver nitrate. The solids were dried at 110° C. The dry material was analyzed for its iodine content using classical method of iodometry employing sodium thiosulphate as titrant and found to contain 0.55% of iodine in it. The composite filtrate was analysed for its potassium iodate content and found to contain 1.20 mg of potassium iodate. The $K^+$ content of the composite filtrate analysed by flame photometer was found to be 10 mg.

Example-3

6 gm of hydrotalcite having molar ratio of $MgO:Al_2O_3$ equal to 6.0, XRD pattern having intensity peaks (A°) 7.77, 3.87, 2.57, 1.53, 1.50, 1.42, and sharp IR absorption peak of interlayer carbonate ions at 1370 cm$^{-1}$, was powdered to pass through 60 BSS mesh and calcined in a furnace at 525° C. for one hour. The calcined hydrotalcite was cooled to 60° C. This was added to 50 ml of 0.01M potassium iodate solution prepared in distilled water which is heated to 60° C. prior to addition. The reacting mass was stirred for five minutes maintaining the said temperature and left to stand for one hour with intermittent stirring for one minute at an interval of 30 minute. The resultant slurry was filtered. The solid separated was washed with 200 ml distilled water till the wash filtrate does not show any silver iodate precipitate with silver nitrate. The solids were dried at 110° C. The dry material was analyzed for its iodine content using classical method of iodometry employing sodium thiosulphate as titrant and found to contain 1.10% of iodine in it. The composite filtrate containing wash water was analysed for its potassium iodate content and found to contain 5.7 mg of potassium iodate in 250 ml of composite filtrate. The K$^+$ content of the composite filtrate analysed by flame photometer was found to be 20 mg of K$^+$.

Example-4

6 gm of hydrotalcite having molar ratio of MgO:Al$_2$O$_3$ equal to 5.5, XRD pattern having intensity peaks (A°) 7.60, 3.82, 2.57, 1.53, 1.50, 1.42, and sharp IR absorption peak of interlayer carbonate ions at 1365 cm$^{-1}$, was powdered to pass through 60 BSS mesh and calcined in a furnace at 500° C. for one hour. The calcined hydrotalcite was cooled to 75° C. This was added to 100 ml of 0.015M potassium iodate solution prepared in distilled water which is heated to 75° C. prior to addition. The reacting mass was stirred for five minutes maintaining the said temperature and left to stand for one hour with intermittent stirring for one minute at an interval of 30 minute. The resultant slurry was filtered. The solid separated was washed with distilled water till the wash filtrate does not show any silver iodate precipitate with silver nitrate. The solids were dried at 110° C. The dry material was analyzed for its iodine content using classical method of iodometry employing sodium thiosulphate as, titrant and found to contain 3.0% of iodine in it. The filtrate was analysed for its potassium iodate content and found that 86% of input iodate was consumed.

Example-5

6 gm of hydrotalcite having molar ratio of MgO:Al$_2$O$_3$ equal to 6.0, XRD pattern having intensity peaks (A°) 7.77, 3.87, 2.57, 1.53, 1.50, 1.42, and sharp IR absorption peak of interlayer carbonate ions at 1370 cm$^{-1}$, was powdered to pass through 60 BSS mesh and calcined in a furnace at 500° C. for seventy five minutes. The calcined hydrotalcite was cooled to 75° C. This was added to 125 ml of 0.021M potassium iodate solution prepared in distilled water which is heated to 75° C. prior to addition. The reacting mass was stirred for five minutes maintaining the said temperature and left to stand for one hour with intermittent stirring for one minute at an interval of 30 minute. The resultant slurry was filtered. The solid separated was washed with distilled water till the wash filtrate does not show any silver iodate precipitate with silver nitrate. The solids were dried at 110° C. The dry material was analyzed for its iodine content using classical method of iodometry employing sodium thiosulphate as titrant and found to contain 5.16% of iodine in it.

Example-6

12 gm of hydrotalcite having molar ratio of MgO:Al$_2$O$_3$ equal to 6.0, XRD pattern having intensity peaks (A°) 7.77, 3.87, 2.57, 1.53, 1.50, 1.42, and sharp IR absorption peak of interlayer carbonate ions at 1370 cm$^{-1}$, was powdered to pass through 60 BSS mesh and calcined in a furnace at 500° C. for one hour. The calcined hydrotalcite was cooled to 65° C. This was added to 100 ml of 0.01M potassium iodate solution prepared in distilled water which is heated to 70° C. prior to addition. The reacting mass was stirred for five minutes maintaining the said temperature and left to stand for one hour with intermittent stirring for one minute at an interval of 30 minute. The resultant slurry was filtered. The solid separated was washed with distilled water till the wash filtrate does not show any silver iodate precipitate with silver nitrate. The solids were dried at 110° C. The dry material was analyzed for its iodine content using classical method of iodometry employing sodium thiosulphate as titrant and found to contain 1.1% of iodine in it.

Example-7

3 gm of hydrotalcite having molar ratio of MgO:Al$_2$O$_3$ equal to 5.5, XRD pattern having intensity peaks (A°) 7.60, 3.82, 2.57, 1.53, 1.50, 1.42, and sharp IR absorption peak of interlayer carbonate ions at 1365 cm$^{-1}$, was powdered to pass through 60 BSS mesh and calcined in a furnace at 500° C. for one hour. The calcined hydrotalcite was cooled to 75° C. This was added to 180 ml of 0.0147M potassium iodate solution prepared in distilled water which is heated to 75° C. prior to addition. The reacting mass was stirred for five minutes maintaining the said temperature and left to stand for one hour with intermittent stirring for one minute at an interval of 30 minute. The resultant slurry was filtered. The solid separated was washed with distilled water till the wash filtrate does not show any silver iodate precipitate with silver nitrate. The solids were dried at 110° C. The dry material was analyzed for its iodine content using classical method of iodometry employing sodium thiosulphate as titrant and found to contain 10.2% of iodine in it. The filtrate was analysed for its potassium iodate content and found that 87% of input iodate was consumed.

Example-8

4 gm of hydrotalcite having molar ratio of MgO:Al$_2$O$_3$ equal to 5.5, XRD pattern having intensity peaks (A°) 7.60, 3.82, 2.57, 1.53, 1.50, 1.42, and sharp IR absorption peak of interlayer carbonate ions at 1365 cm$^{-1}$, was powdered to pass through 60 BSS mesh and calcined in a furnace at 500° C. for one hour. The calcined hydrotalcite was cooled to 75° C. This was added to 180 ml of 0.0155M potassium iodate solution prepared in distilled water, which is heated to 75° C. prior to addition. The reacting mass was stirred for five minutes maintaining the said temperature and left to stand for one hour with intermittent stirring for one minute at an interval of 30 minute. The resultant slurry was filtered. The solid separated was washed with distilled water till the wash filtrate does not show any silver iodate precipitate with silver nitrate. The solids were dried at 110° C. The dry material was analyzed for its iodine content using classical method of iodometry employing sodium thiosulphate as titrant and found to contain 8.15% of iodine in it. The filtrate was analysed for its potassium iodate content and found that 88% of input iodate was consumed.

Example-9

1.43 gm of iodate containing hydrotalcite prepared in Example-1 was mixed thoroughly and uniformly with 1 kg of solar salt, which is ground and sieved to obtain fraction of −32+70 BSS mesh. The salt used was having impurity of Ca—0.09% (w/w), Mg—0.065% (w/w), $SO_4$—0.15% (w/w), Insoluble—0.05% (w/w), Moisture—0.53% (w/w). The iodized salt so prepared contains 30 ppm of iodine. One of the best brand iodized salt was obtained from the market and used as control salt sample, which was analyzed for its iodine content and found to contain 39 ppm of iodine. 50 gm of salt samples prepared from above were kept in oven at 100° C. for 96 hours and iodine content was measured every 24 hours. The salt containing iodine in the form of hydrotalcite equivalent to 30 ppm of iodine retained all the iodine without any loss. The branded salt, which contained 39 ppm of iodine, found to contain 31 ppm of iodine at the end of 96 hours incurring loss of iodine of 21%.

THE ADVANTAGES OF THE PRESENT INVENTION ARE i. The invention provides a stable iodizing compound for imparting enhanced stability of iodine in iodised salt.
ii. The iodine stability in iodizing agent is also enhanced in presence of moisture, chemical impurities, and under varying temperature conditions.
iii. The iodizing agent is prepared using pharma grade synthetic hydrotalcite.
iv. The iodizing agent having enhanced stability of iodine can be prepared employing simple unit operations in cost effective manner.
v. The iodizing agent is easily and uniformly mixed in a dry state with the edible salt

We claim:
1. A method for the preparation of an iodizing agent that offers stability of iodine in formulation of iodised salt, the method comprising:
   (i) grinding pharma grade hydrotalcite to obtain hydrotalcite powder;
   (ii) calcining the hydrotalcite powder to obtain calcined hydrotalcite;
   (iii) cooling the calcined hydrotalcite to obtain solid synthetic hydrotalcite with an interlayer space within said solid synthetic hydrotalcite;
   (iv) heating an aqueous water soluble alkali metal salt solution;
   (v) adding calculated quantity of the solid synthetic hydrotalcite obtained in step (iii) into the water soluble alkali metal salt solution prepared in step (iv) under agitation for uniform dispersion to obtain a reaction mixture;
   (vi) maintaining the temperature of the reaction mixture in the range of 60 to 80° C. while stirring the reaction mixture to obtain a slurry comprising solid synthetic hydrotalcite and fluid water soluble alkali metal salt solution;
   (vii) aging the slurry for a period between 30 to 60 minutes and intermittently stirring for 1 minute at an interval of 30 minutes for effective contact and substitution of anions in the interlayer space;
   (viii) filtering the slurry to remove the fluid water soluble alkali metal salt solution to obtain a solid synthetic hydrotalcite cake, and washing the solid synthetic hydrotalcite cake so obtained with distilled water to remove adhering salts that formed during steps v, vi, viii;
   (ix) drying the solid synthetic hydrotalcite cake to get the iodizing agent.

2. A method as claimed in claim 1 wherein the pharma grade hydrotalcite has $MgO:Al_2O_3$ molar ratio of in the range of 7.7 to 4.6 and sharp IR absorption peak of interlayer carbonate ions at ca. 1360 $cm^{-1}$.

3. A method as claimed in claim 1 wherein the solid synthetic hydrotalcite is ground to pass through 60 BSS mesh.

4. A method as claimed in claim 1 wherein the water soluble alkali metal salt is potassium iodate.

5. A method as claimed in claim 1 wherein the hydrotalcites powder is calcined at a temperature in the range of 450° C. to 550° C. for 30 to 75 minutes followed by cooling to 60-80° C.

6. A method as claimed in claim 1 wherein a concentration of water soluble alkali metal salt in the water soluble alkali metal salt solution is in the range of 0.005 to 0.022 molar.

7. A method as claimed in claim 1 wherein the water soluble alkali metal salt solution is heated in the range 60-80° C. prior to addition of solid synthetic hydrotalcite.

8. A method as claimed in claim 4 wherein the iodine content in the iodizing agent is in the range of 0.5-10.0% (w/w).

9. A method as claimed in claim 4 wherein the drying step involves drying the solid synthetic hydrotalcite in an oven at 80-110° C. to expel all moisture to obtain the iodizing agent.

10. A method as claimed in claim 4 wherein the iodine content of the iodizing agent is about 30 ppm.

* * * * *